United States Patent [19]
Bedeschi et al.

[11] Patent Number: 5,990,120
[45] Date of Patent: Nov. 23, 1999

[54] HEXACYCLIC CAMPTOTHECIN ANALOGUES, AND PROCESS FOR PREPARING THEM

[75] Inventors: Angelo Bedeschi, Milan; Ilaria Candiani, Varese; Franco Zarini, Milan, all of Italy

[73] Assignee: Pharmacia & Upjohn S.p.A., Milan, Italy

[21] Appl. No.: 08/894,794

[22] PCT Filed: Dec. 17, 1996

[86] PCT No.: PCT/EP96/05752

§ 371 Date: Sep. 10, 1997

§ 102(e) Date: Sep. 10, 1997

[87] PCT Pub. No.: WO97/25332

PCT Pub. Date: Jul. 17, 1997

[30]      Foreign Application Priority Data

Jan. 10, 1996 [GB] United Kingdom ............ 9600438

[51] Int. Cl.⁶ .............. A61K 31/435; C07D 491/22; C07D 498/22; C07D 513/22
[52] U.S. Cl. .............................. 514/279; 546/41
[58] Field of Search .................... 546/41; 514/279

[56]           References Cited

U.S. PATENT DOCUMENTS

| 4,981,968 | 1/1991 | Wall et al. ............... 546/41 |
| 5,614,628 | 3/1997 | Cabri et al. ............. 546/48 |
| 5,648,534 | 7/1997 | Igarashi et al. ......... 548/217 |
| 5,670,500 | 9/1997 | Berges et al. ........... 546/41 |

*Primary Examiner*—Richard L. Raymond
*Attorney, Agent, or Firm*—Oblon, Spivak, McClelland, Maier & Neustadt, P.C.

[57]           ABSTRACT

The present invention relates to novel hexacyclic camptohecin analogues, having a five-membered aza-heterocycle fused to ring (A) of camptothecin at positions 9 and 10. Such compounds possess high antitumor activity by inhibition of topoisomerase (I).

10 Claims, No Drawings

HEXACYCLIC CAMPTOTHECIN ANALOGUES, AND PROCESS FOR PREPARING THEM

The present application is a 371 of PCT/EP95/05752, filed Dec. 17, 1996.

The present invention relates to new hexacyclic camptothecin analogues possessing antitumor activity, to a process for preparing the same, and to pharmaceutical compositions containing them.

It is well known in the art that camptothecin and some of its analogues display potent antitumor activity by inhibition of topoisomerase I, an enzyme involved in some important cellular functions and in cellular growth (see for instance Wani et al., *J. Med. Chem.*, 1987, 30, 1774; Hsiang et al., *Cancer Res.*, 1989, 49, 4385; *Cancer Res.*, 1989, 49, 1465). Anticancer activity of camptothecin both in vitro and in vivo are significantly greater for the lactone versus the carboxylate form (as disclosed for instance by W. J. Slichenmyer, et al., in "The Current Status of Camptothecin Analogues as Antitumor Agents", *J. Natl. Cancer Inst.*, 1993, 85, 271–291, and the references cited therein), since a closed α-hydroxy lactone ring is an important structural requirement for both passive diffusion of drug into cancer cells, as well as for a successful drug interaction with the pharmacological target. It has been recently reported that, in the presence of biologically relevant levels of human albumin, the biologically active form of camptothecin has a very short half-life (about 12 min), and 2 hours after drug addition to human plasma, more than 99% of the drug has converted to camptothecin carboxylate, the biologically inactive and potentially toxic form of the drug (see Burke, G. T., and Mi, Z. "The Structural Basis of Camptothecin Interactions with Human Serum Albumin: Impact on Drug Stability", *J. Med. Chem.*, 1994, 37, 40–46). Therefore, a need is felt of finding new camptothecin derivatives having high intrinsic potency and which can gain stability in the presence of serum albumine.

M. C. Wani et al. report in *J. Med. Chem.*, 1986, 29, 2358–2363, that monosubstitution by $NH_2$ or OH at positions 9, 10, or 11 in ring A of camptothecin yields compounds with antileukemic activity much higher than the parent compound camptothecin. On the contrary, disubstitution in ring A greatly reduces activity. Particularly, compounds with substituents at both positions 9 and 10 demonstrate a marked drop in activity and/or potency, probably due to steric interaction.

The Applicant has now surprisingly found that certain hexacyclic camptothecin analogues as defined hereinunder, having a five-membered aza-heterocycle fused to ring A of camptothecin at positions 9 and 10, possess high antitumor activity.

The present invention therefore provides a hexacyclic camptothecin analogue of formula (Ia)

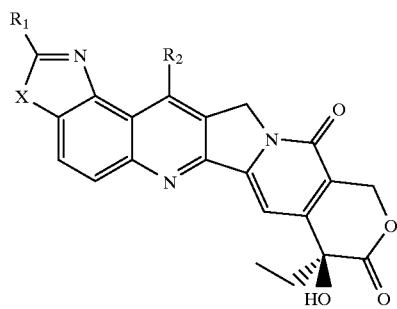

(Ia)

wherein:

$R_1$ is selected from:
hydrogen;
an optionally substituted $C_1$–$C_6$ alkyl such as a phenyl $C_1$–$C_6$ alkyl;
a $C_3$–$C_7$ cycloalkyl;
an optionally substituted phenyl;
a —$NR_3R_4$ group, wherein $R_3$ and $R_4$ are, each independently:
hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; or a benzoyloxycarbonyl; or $R_3$ and $R_4$, combined together with the nitrogen atom to which they are linked, form a 3–7 membered, saturated or unsaturated, optionally substituted, hetero-monocyclic ring;
a —$OR_5$ group, wherein $R_5$ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; or a benzoyloxycarbonyl; and
a —$SR_6$ group, wherein $R_6$ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_3$–$C_7$ alkanoyl; an optionally substituted benzoyl; an optionally substituted $C_1$–$C_6$ alkoxycarbonyl; or a benzoyloxycarbonyl;

$R_2$ is selected from:
hydrogen; a $C_1$–$C_6$ alkyl; a $C_3$–$C_7$ cycloalkyl; and a phenyl $C_1$–$C_6$ alkyl; and
X is selected from:
an oxygen atom;
a sulfur atom;
a —$NR_7$— group, wherein $R_7$ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; a benzoyloxycarbonyl; an optionally substituted $C_1$–$C_6$ alkylsulfonyl; an optionally substituted $C_6$–$C_{10}$ arylsulfonyl;

or a hexacyclic camptothecin analogue of formula (Ib):

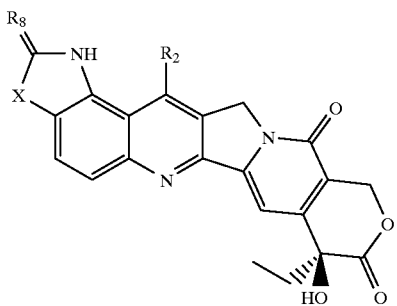

(Ib)

wherein:

$R_8$ is selected from:
  an oxygen atom;
  a sulfur atom;
  a =$NR_9$ group, wherein $R_9$ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; a benzoyloxycarbonyl;

$R_2$ is selected from:
  hydrogen; a $C_1$–$C_6$ alkyl; a $C_3$–$C_7$ cycloalkyl; and a phenyl $C_1$–$C_6$ alkyl; and X is selected from:
  an oxygen atom;
  a sulfur atom;
  a —$NR_7$— group, wherein $R_7$ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; a benzoyloxycarbonyl; an optionally substituted $C_1$–$C_6$ alkylsulfonyl; an optionally substituted $C_6$–$C_{10}$ arylsulfonyl.

Within the scope of the present invention are also the pharmaceutically acceptable salts of the compounds of formula (Ia) and (Ib).

Pharmaceutically acceptable salts include salts with pharmaceutically acceptable acids, both inorganic acids such as, e.g. hydrochloric, sulfuric, phosphoric, diphosphoric, hydrobromic or nitric acid, and organic acids such as, e.g. citric, fumaric, maleic, malic, ascorbic, succinic, tartaric, benzoic, acetic methanesulfonic, ethanesulfonic, benzenesulfonic or p-toluensulfonic acid.

As used herein, the terms "each independently" or the equivalents thereof are employed to describe a number of possible structural variations.

In the formulae of the present specification, a dotted line ......ııııı indicates a substituent below the plane of the ring; a wedged line ◀ indicates a substituent above the plane of the ring.

Unless herein otherwise specified, in the present specification the hydrocarbon chain of an alkyl, cycloalkyl, phenylalkyl, alkanoyl, alkoxycarbonyl, or alkylsulfonyl group is a linear or branched unsubstituted alkyl chain.

With reference to both formulae (Ia) and (Ib), preferred meanings of the various substituents are as follows.

An alkyl group is preferably a $C_1$–$C_4$ alkyl group, for example methyl, ethyl, n-propyl, isopropyl, n-butyl, isobutyl, sec-butyl or tert-butyl. When an alkyl group is substituted, it is preferably a $C_1$–$C_4$ alkyl group substituted by one or more groups selected from halogen atoms, preferably chlorine or fluorine, and optionally protected amino, carboxy or hydroxy groups. A particularly preferred substituted alkyl group is phenyl $C_1$–$C_6$ alkyl.

Protecting groups for such moieties can be selected from those known in the art (see, for instance, Green, W. T., Wuts, P. G. M., "Protective Groups in Organic Synthesis", Wiley-Interscience, John Wiley & Sons, New York, N.Y.).

For instance, for the amino moiety preferred protecting groups are e.g.: acetyl, propanoyl, butanoyl, optionally substituted benzoyl, optionally substituted $C_1$–$C_4$ alkoxycarbonyl, or optionally substituted phenyl $C_1$–$C_4$ alkoxycarbonyl. Protecting groups for the carboxy or hydroxy moiety are, for example, ester groups, such as $C_1$–$C_6$ alkyl, $C_3$–$C_6$ alkenyl, benzyl, nitrobenzyl or benzydryl ester groups. The most preferred protecting groups for the carboxy moiety include methyl, ethyl, tert-butyl, allyl, methallyl, benzyl, o- or p-nitrobenzyl and benzydryl ester groups.

A cycloalkyl group is preferably a $C_3$–$C_6$ cycloalkyl group such as, e.g., cyclopropyl, cyclobutyl, cyclopentyl or cyclohexyl. In the present specification, the alkyl portion of a phenyl $C_1$–$C_6$ alkyl, $C_1$–$C_6$ alkanoyl, $C_1$–$C_6$ alkoxycarbonyl, or $C_1$–$C_6$ alkylsulfonyl group has the same preferred meanings as indicated above for the $C_1$–$C_6$ alkyl groups. When substituted, a phenyl or a benzoyl group has one or more hydrogen atoms on the ring substituted by e.g.: $C_1$–$C_6$ alkyl, $C_1$–$C_6$ alkoxy, $C_1$–$C_6$ alkanoyloxy, amino, nitro, or halogen.

Preferably, phenyl or benzoyl groups are substituted by one or more groups selected from: $C_1$–$C_4$ alkyl, $C_1$–$C_4$ alkoxy, amino, nitro, or halogen. More preferably phenyl or benzoyl groups are substituted by: methyl, ethyl, propyl, methoxy, ethoxy, propoxy, isopropoxy, chlorine, or fluorine.

A substituted $C_1$–$C_6$ alkoxycarbonyl group is, preferably, trichloroethoxycarbonyl.

An alkylsulfonyl group is preferably a $C_1$–$C_4$ alkylsulfonyl group, more preferably it is methanesulfonyl or ethanesulfonyl. A substituted alkylsulfonyl group is preferably a $C_1$–$C_4$ alkylsulfonyl group substituted by one or more halogen atoms, preferably one or more fluorine atoms. More preferably, it is trifluoromethanesulfonyl or trifluoroethanesulfonyl. As optionally substituted $C_6$–$C_{10}$ arylsulfonyl groups, particularly preferred are benzenesulfonyl, p-toluenesulfonyl, p-fluoro-benzenesulfonyl, p-nitrobenzenesulfonyl, and naphthalenesulfonyl groups.

$R_1$ is preferably methyl, butyl, phenyl or amino.

$R_2$ is preferably: hydrogen, methyl, ethyl, n-propyl, butyl, isopropyl, isobutyl, sec-butyl, tert-butyl, cyclopropyl, cyclobutyl, cyclopentyl, cyclohexyl, benzyl, phenylethyl, phenylpropyl or phenylbutyl. The most preferred meanings of $R_2$ are hydrogen, methyl, ethyl, or tert-butyl.

X is preferably an oxygen atom or a sulfur atom.

When, in a compound of formula (Ia), $R_1$ is a group —$NR_3R_4$ in which $R_3$ and $R_4$, combined together with the nitrogen atom to which they are linked, form a 3–7 membered, saturated or unsaturated, optionally substituted, heteromonocyclic ring the ring may be, for example, a 3,4,5,6 or 7 membered ring. Preferably, it is, for example, a pirrolidinyl or a piperidyl ring.

A first preferred class of compounds according to the present invention are those of formula (Ia) wherein:

$R_1$ is selected from:
  hydrogen;
  $C_1$–$C_6$ alkyl;
  an optionally substituted phenyl; and a —NR$_3$R$_4$ group, wherein R$_3$ and R$_4$ are, each independently:
  hydrogen; a C$_1$–C$_6$ alkyl; or a C$_1$–C$_6$ alkanoyl;
R$_2$ is selected from:
  hydrogen; and
  a C$_1$–C$_6$ alkyl;
X is selected from:
  an oxygen atom; and
  a sulfur atom;
and pharmaceutically acceptable salts thereof.

A second preferred class of compounds according to the present invention are those of formula (Ib) wherein:
R$_8$ is selected from:
  an oxygen atom; and
  a —NR$_9$— group, wherein R$_9$ is: hydrogen; a C$_1$–C$_6$ alkyl; or a C$_1$–C$_6$ alkanoyl;
R$_2$ is selected from:
  hydrogen; and
  a C$_1$–C$_6$ alkyl;
X is selected from:
  an oxygen atom; and
  a sulfur atom;
and pharmaceutically acceptable salts thereof.

Examples of preferred compounds of formula (Ia) are listed in the following Table 1, wherein the symbol Me, n-Bu and Ph stand respectively for methyl, n-butyl and phenyl. The tabulated compounds are identified by a number and their corresponding chemical names are reported under each table.

TABLE 1

| Compound | R$_1$ | R$_2$ | X |
|---|---|---|---|
| 1 | H | H | O |
| 2 | Me | H | O |
| 3 | n-Bu | H | O |
| 4 | Ph | H | O |
| 5 | H | Et | O |
| 6 | Me | Et | O |
| 7 | n-Bu | Et | O |
| 8 | Ph | Et | O |
| 9 | H | H | S |
| 10 | Me | H | S |
| 11 | n-Bu | H | S |
| 12 | Ph | H | S |
| 13 | NH$_2$ | H | S |
| 14 | NHCOCH$_3$ | H | S |
| 15 | H | Et | S |
| 16 | Me | Et | S |
| 17 | n-Bu | Et | S |
| 18 | Ph | Et | S |

Chemical names of the above tabulated compounds of formula (Ia) are as follows:
1) oxazolo[4,5-i]camptothecin;
2) 2-methyl-oxazolo[4,5-i]camptothecin;
3) 2-butyl-oxazolo[4,5-i]camptothecin;
4) 2-phenyl-oxazolo[4,5-i]camptothecin;
5) 7-ethyl-oxazolo[4,5-i]camptothecin;
6) 7-ethyl-2-methyl-oxazolo[4,5-i]camptothecin;
7) 7-ethyl-2-butyl-oxazolo[4,5-i]camptothecin;
8) 7-ethyl-2-phenyl-oxazolo[4,5-i]camptothecin;
9) thiazolo[4,5-i]camptothecin;
10) 2-methyl-thiazolo[4,5-i]camptothecin;
11) 2-butyl-thiazolo[4,5-i]camptothecin;
12) 2-phenyl-thiazolo[4,5-i]camptothecin;
13) 2-amino-thiazolo[4,5-i]camptothecin;
14) 2-acetamido-thiazolo[4,5-i]camptothecin;
15) 7-ethyl-thiazolo[4,5-i]camptothecin;
16) 7-ethyl-2-methyl-thiazolo[4,5-i]camptothecin;
17) 7-ethyl-2-butyl-thiazolo[4,5-i]camptothecin; and
18) 7-ethyl-2-phenyl-thiazolo[4,5-i]camptothecin.

Examples of preferred compounds of formula (Ib) are listed in the following Table 2, wherein the symbol Me stands for methyl.

TABLE 2

| Compound | R$_8$ | R$_2$ | X |
|---|---|---|---|
| 19 | O | H | O |
| 20 | NH | H | O |
| 21 | NMe | H | O |
| 22 | O | Et | O |
| 23 | NH | Et | O |
| 24 | NMe | Et | O |
| 25 | O | H | S |
| 26 | NH | H | S |
| 27 | NMe | H | S |
| 28 | O | Et | S |
| 29 | NH | Et | S |
| 30 | NMe | Et | S |

Chemical names of the above tabulated compounds of formula (Ib) are as follows:
19) oxazolidino[4,5-i]camptothecin-2-one;
20) 2-imino-oxazolidino[4,5-i]camptothecin;
21) 2-methylimino-oxazolidino[4,5-i]camptothecin;
22) 7-ethyl-oxazolidino[4,5-i]camptothecin-2-one;
23) 7-ethyl-2-imino-oxazolidino[4,5-i]camptothecin;
24) 7-ethyl-2-methylimino-oxazolidino[4,5-i]camptothecin;
25) thiazolidino[4,5-i]camptothecin-2-one;
26) 2-imino-thiazolidino[4,5-i]camptothecin;
27) 2-methylimino-thiazolidino[4,5-i]camptothecin;
28) 7-ethyl-thiazolidino[4,5-i]camptothecin-2-one;
29) 7-ethyl-2-imino-thiazolidino[4,5-i]camptothecin; and
30) 7-ethyl-2-methylimino-thiazolidino[4,5-i]camptothecin.

The compounds of formula (Ia) and (Ib) of the present invention may be prepared by a process which is exemplified in the following Scheme A wherein the meanings of R$_1$, R$_2$ and X are as defined above.

Scheme A

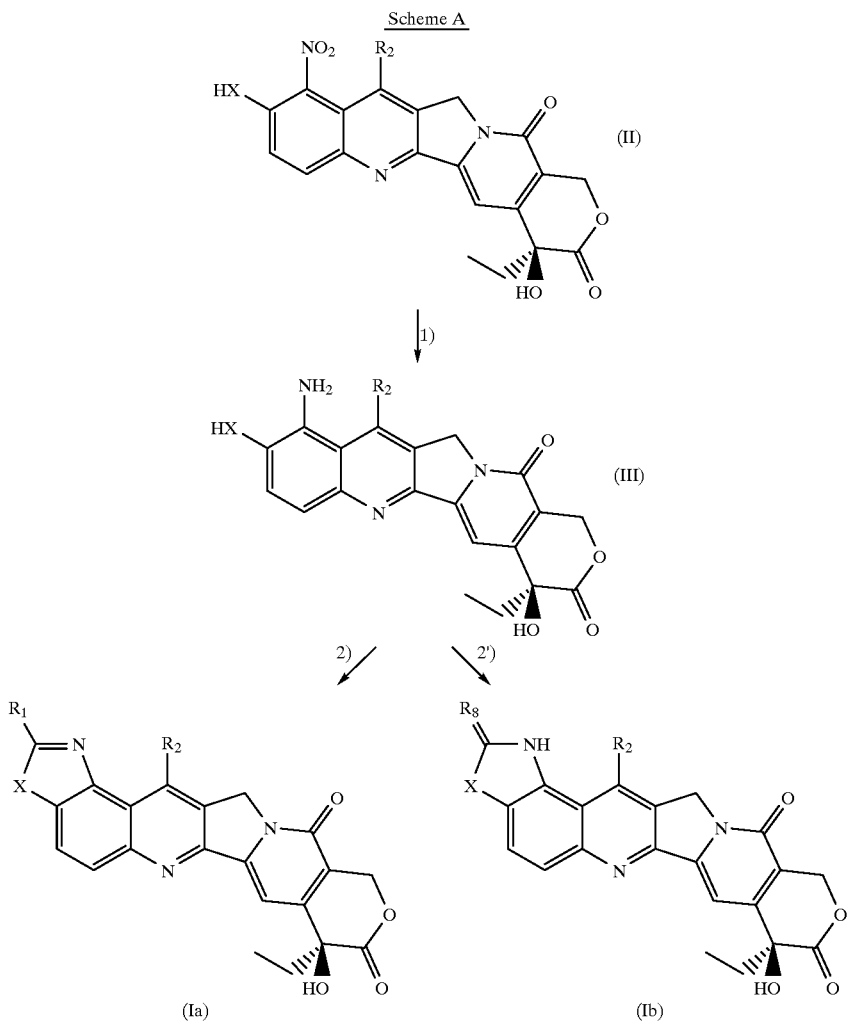

According to the above Scheme A the compounds of the invention can be prepared by a process comprising:

1) reducing a compound of formula (II):

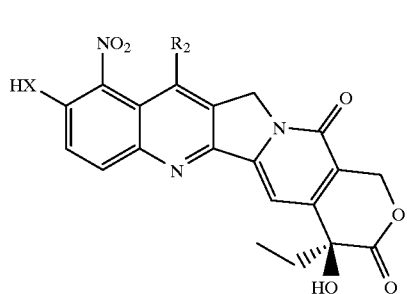
(II)

wherein:
R$_2$ is selected from:
  hydrogen; a C$_1$–C$_6$ alkyl; a C$_3$–C$_7$ cycloalkyl; and a phenyl C$_1$–C$_6$ alkyl; and
X is selected from:
  an oxygen atom;
  a sulfur atom;

a —NR$_7$— group, wherein R$_7$ is: hydrogen; an optionally substituted C$_1$–C alkyl such as a phenyl C$_1$–C$_6$ alkyl; a C$_3$–C$_7$ cycloalkyl; an optionally substituted phenyl; a C$_1$–C$_6$ alkanoyl; an optionally substituted benzoyl; an optionally substituted C$_1$–C$_6$ alkoxycarbonyl; a benzoyloxycarbonyl; an optionally substituted C$_1$–C$_6$ alkylsulfonyl; an optionally substituted C$_6$–C$_{10}$ arylsulfonyl;

so obtaining a compound of formula (III):

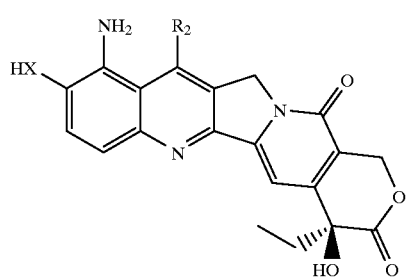
(III)

wherein R$_2$ and X are as defined above;

2) either (a): reacting a compound of formula (III) with a compound of formula (IV):

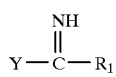

wherein:

R₁ is selected from:
 hydrogen;
 an optionally substituted $C_1$–$C_6$ alkyl such as phenyl $C_1$–$C_6$ alkyl;
 a $C_3$–$C_7$ cycloalkyl;
 an optionally substituted phenyl;
 a —NR₃R₄ group, wherein R₃ and R₄ are, each independently: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; or a benzoyloxycarbonyl; or R₃ and R₄, combined together with the nitrogen atom to which they are linked, form a 3–7 membered, saturated or unsaturated, optionally substituted, heteromonocyclic ring;
 a —OR₅ group, wherein R₅ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_3$–$C_6$ alkoxycarbonyl; or a benzoyloxycarbonyl; and
 a —SR₆ group, wherein R₆ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; or a benzoyloxycarbonyl; and Y is a leaving group;

so obtaining a compound of formula (Ia) as defined above;

or (b):
 reacting a compound of formula (III) with a compound of formula (V)

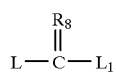

wherein:

R₈ is selected from:
 an oxygen atom;
 a sulfur atom; and
 a =NR, group, wherein R₉ is: hydrogen; an optionally substituted $C_1$–$C_6$ alkyl such as a phenyl $C_1$–$C_6$ alkyl; a $C_3$–$C_7$ cycloalkyl; an optionally substituted phenyl; a $C_1$–$C_6$ alkanoyl; an optionally substituted benzoyl; an optionally substituted $C_1$–$C_6$ alkoxycarbonyl; a benzoyloxycarbonyl; and L and L₁, each independently, are leaving groups; so obtaining a compound of formula (Ib) as defined above; and 3) optionally salifying the thus obtained compound of formula (Ia) or (Ib) to give a pharmaceutically acceptable salt thereof.

The leaving groups L and L₁ can be, for example, halogen atoms, alkoxy (e.g. methoxy, ethoxy, or trichloroethoxy), phenoxy, or imidazole groups. The leaving group Y is, for example, a halogen atom, e.g. chlorine, or an alkoxycarbonyl group, e.g. an ethoxycarbonyl group.

The reaction of the above step 1) is preferably carried out by reducing the compound (II) with a reducing agent in a suitable solvent, in the presence of a suitable catalyst.

Suitable reducing agents are, e.g., molecular hydrogen or hydrogen sources, such as, for instance, triethylammonium formate, formic acid, tributyltin hydride, cyclohexadiene, etc., in a suitable solvent, such as dimethylformamide (DMF), methanol, acetic acid, chloroform, dioxane, or mixtures thereof. Typically, the reaction temperature is from about 0° C. to 100° C. Typically, the reaction is conducted for a time of from 1 hour to 3 days. Typically, the reaction takes place at a pressure of from 1 atm to 100 atm. Suitable catalysts for the above said reduction include transition metals, such as, e.g., palladium, platinum, rhodium, nickel, ruthenium, or mixtures thereof.

The reduction step 1) may be also carried out as described by J. March in "Advanced Organic Chemistry", 3rd Edition, p. 1103, or, for instance, with a reducing metal or metal salt, such as $SnCl_2$, Zn or Fe and salts thereof, in a suitable solvent, such as, e.g., diluted aqueous protic acids, e.g. HCl, water, ethanol, methanol, or mixtures thereof, at a temperature of from −20° C. to +60° C., for a time of from few minutes to several days.

The reaction of a compound of formula (III) with a compound of formula (IV) is preferably carried out by reacting compound (III) with compound (IV) in a suitable solvent. Typically, the reaction temperature is from about −20° C. to about 200° C., preferably from about 20° C. to about 100° C. Typically, the reaction is conducted for a time which may vary from about a few minutes to several days, e.g. from 5 minutes to 3 days, preferably from about one hour to about one day, optionally in the presence of a suitable organic or inorganic base. Suitable solvents include dimethylformamide (DMF), acetonitrile, dimethylsulfoxide (DMSO), chloroform, dioxane, tetrahydrofuran (THF), or mixtures thereof.

Suitable inorganic bases can be selected, for instance, from alkali or alkaline earth metal salts, such as, for example, $NaHCO_3$, $Na_2CO_3$, or NaOAc.

Suitable organic bases may be, for example, trialkylamines, such as triethylamine or diisopropylethylamine; or heteroaromatic bases such as pyridine, or 2,6-$C_1$–$C_6$-alkyl substituted pyridines, e.g. 2,6-lutidine.

The reaction of a compound of formula (III) with a compound of formula (V) may be carried out, for example, by reacting compound (III), dissolved in a suitable solvent, with compound (V). Suitable solvents include ethyl chlorocarbonate, diphenylcarbonate, or trichloroethylchloro-carbonate. Typically, the reaction temperature is from −20° C. to 200° C., and preferably from 20° C. to 100° C. Typically, the reaction is conducted for a time of from 5 minutes to several days, and preferably from about one hour to about ten hours.

The starting compounds of formula (II) and (III) have a 20(S)-configuration which is retained throughout the process leading to the compounds of formula (Ia) or (Ib) with the same 20(S)-configuration, and substantially free of the corresponding 20(R) -isomers.

However, said process may be applied to a racemic mixture of a compound of formula (II) and the corresponding 20(R)-isomer. In that case, a racemic mixture of a compound of formula (Ia) or (Ib) and the corresponding 20(R)-isomer is obtained.

The starting materials used in the process of the present invention are known compounds, or may be obtained following known methods, or by analogy from known methods. For instance, 9-amino-10-hydroxy-camptothecin and 9-nitro-10-hydroxy-camptothecin may be prepared according to Wani, M. C. et al., *J. Med. Chem.*, 1986, 29, 2358–2363.

The compounds of formula (Ia) or (Ib) according to the present invention are endowed with antitumor activity, for example against leukaemia and solid tumours, such as colon and rectal tumours. The antitumor activity of the compounds of the present invention is demonstrated, for example, by the fact that they have been found to possess antileukaemic activity when tested according to the method described in *J. Med. Chem.*, 1993, 36, 2689, using the L1210 murine lymphoid leukaemia model.

The present invention also provides pharmaceutical compositions containing an effective amount of at least one of the hexacyclic camptothecin analogues of formula (Ia) or (Ib) as defined above. Mammalian animals such as humans are treatable with such compositions. Typical in vivo doses are from 0.1 to 60 mg of camptothecin analog per kg of body weight, preferably from 1 to 40 mg/kg.

The compositions of the present invention comprise conventional pharmaceutically compatible binding agents, and/or adjuvants materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred way of administration of the compounds of the present invention is orally. Oral compositions generally include an inert diluent or an edible carrier, and may be enclosed in gelatin capsules or compressed into tablets. For the purpose of oral therapeutic administration, the aforesaid compounds may be incorporated with excipients and used in the form of tablets, capsules, elixirs, syrups, and the like. The amount of active compound contained in such preparations can be varied in a wide range, depending upon the particular composition. Such amount is generally of at least 0.1 by weight of active compound.

Tablets, pills, capsules, troches and the like may contain one or more of the following ingredients: a binder, such as microcrystalline cellulose, gumtragacanth, or gelatin; an excipient, such as starch or lactose; a disintegrating agent such as alginic acid, Primogel (Primogel is a Registered Trade Mark), corn starch, and the like; a lubricant, such as magnesium stearate or Sterotes (Sterotes is a Registered Trade Mark); a glidant, such as colloidal silica; a sweetening agent, such as sucrose or saccharin, and/or a flavouring agent, such as peppermint, methyl salicylate, orange flavouring, and the like.

When the dosage unit form is a capsule, it may contain, in addition to the above additives, a liquid carrier such as a fatty oil. Other dosage unit forms may include different materials which are able to modify the physical form of the dosage unit, for example, a coating material. Thus, tablets or pills may be coated with sugar shellac, or other enteric coating agents. A syrup may contain, in addition to the active compounds, sucrose as sweetening agent and conventional preservatives, dyes, colouring, and flavours. Material used in preparing these various compositions should be pharmaceutically pure and non-toxic in the used amounts.

For the purpose of parenteral therapeutic administration, the active ingredient may be incorporated into a solution or suspension. Such solutions or suspensions may include the following components: a sterile diluent, such as water for injection, saline solution, fixed oils, polyethylene glycols, glycerine, propylene glycol, or other synthetic solvents; antibacterial agents, such as benzyl alcohol or methyl parabens; antioxidants, such as ascorbic acid or sodium bisulfite; chelating agents, such as ethylenediaminetetraacetic acid; buffering agents, such as acetates, citrates or phosphates; and agents for adjusting tonicity, such as sodium chloride or dextrose. The parenteral preparation can be enclosed in ampoules, disposable syringes, or multiple dose vials made of glass or plastic.

The dosage values will vary with the specific severity of the disease condition to be alleviated. It is to be understood that for any particular subject, specific dosage regimens should be adjusted to the individual need and the professional judgement of the person administering or supervising the administration of the aforesaid compound. It is to be further understood that the dosages set forth herein are exemplary only, and they do not limit the scope of the present invention. The dosages may be administered in a sole step, or may be divided into a number of smaller doses to be administered at varying time intervals.

The following examples are given to better illustrate the present invention, and cannot be construed as a limitation of the scope of the invention itself.

EXAMPLE 1

Oxazolo[4,5-i]camptothecin (Compound 1))

To a solution of 9-nitro-10-hydroxy camptothecin (0.5 g) in DMF (50 mL), Pd supported on carbon (Pd/C) (70 mg) was added. The mixture was then hydrogenated in hydrogen atmosphere at room temperature and atmospheric pressure for two hours. The catalyst was filtered off and carefully washed with portions of DMF. The solution was then treated with freshly prepared ethylformimidate (3 g). The mixture was stirred overnight, and then evaporated in vacuo. The residue was taken-up with water/CHCl$_3$. The organic layer was dried, and evaporated in vacuo. The residue was taken-up with EtOH, filtered and dried to afford the title product as a solid (0.2 g).

NMR (DMSO-d$_6$) d (ppm): 0.87 (3H, t, J=7.3 Hz); 1.85 (2H, m); 5.29 (2H, s); 5.42 (2H, s); 6.52 (1H, s); 7.32 (1H, s); 8.18 (1H, d, J=9.2 Hz); 8.29 (1H, d, J=9.2 Hz); 9.02 (1H, s); 9.07 (1H, s).

MS (FD)=389.

By analogy using the appropriate reagents the following compounds were prepared (see Table 1):
2) 2-methyl-oxazolo[4,5-i]camptothecin;
3) 2-butyl-oxazolo[4,5-i]camptothecin;
4) 2-phenyl-oxazolo[4,5-i]camptothecin;
5) 7-ethyl-oxazolo[4,5-i]camptothecin;
6) 7-ethyl-2-methyl-oxazolo[4,5-i]camptothecin;
7) 7-ethyl-2-butyl-oxazolo[4,5-i]camptothecin;
8) 7-ethyl-2-phenyl-oxazolo[4,5-i]camptothecin;
9) thiazolo[4,5-i]camptothecin;
10) 2-methyl-thiazolo[4,5-i]camptothecin;
11) 2-butyl-thiazolo[4,5-i]camptothecin;
12) 2-phenyl-thiazolo[4,5-i]camptothecin;
13) 2-amino-thiazolo[4,5-i]camptothecin;
14) 2-acetamido-thiazolo[4,5-i]camptothecin;
15) 7-ethyl-thiazolo[4,5-i]camptothecin;
16) 7-ethyl-2-methyl-thiazolo[4,5-i]camptothecin;
17) 7-ethyl-2-butyl-thiazolo[4,5-i]camptothecin; and
18) 7-ethyl-2-phenyl-thiazolo[4,5-i]camptothecin.

EXAMPLE 2

Oxazolidino[4,5-i]camptothecin-2-one (Compound 19)

To a solution of 9-nitro-10-hydroxy-camptothecin (0.2 g) in THF (50 mL), Pd/C catalyst (100 mg) was added. The mixture was then hydrogenated in hydrogen atmosphere at room temperature and atmospheric pressure for two hours. The catalyst was filtered off and carefully washed with portions of THF. Carbonyldiimidazole (0.24 g) was added and the mixture was heated to 70° C. for four hours. The solution was evaporated in vacuo and the crude reaction mixture was purified by column chromatography, to yield 0.1 g of the title product.

NMR (DMSO-$d_6$) d (ppm): 0.85 (3H, t, J=7.3 Hz); 1.83 (2H, m); 5.31 (2H, s); 5.39 (2H, s); 6.50 (1H, s); 7.29 (1H, s); 7.89 (2H, m); 8.63 (1H, s); 12.6 (1H, bs).

MS (FD) =405.

By analogous process using the suitable reagents the following compounds were prepared (see Table 2):
20) 2-imino-oxazolidino[4,5-i]camptothecin;
21) 2-methylimino-oxazolidino[4,5-i]camptothecin;
22) 7-ethyl-oxazolidino[4,5-i]camptothecin-2-one;
23) 7-ethyl-2-imino-oxazolidino[4,5-i]camptothecin;
24) 7-ethyl-2-methylimino-oxazolidino[4,5-i]camptothecin;
25) thiazolidino[4,5-i]camptothecin-2-one;
26) 2-imino-thiazolidino[4,5-i]camptothecin;
27) 2-methylimino-thiazolidino[4,5-i]camptothecin;
28) 7-ethyl-thiazolidino[4,5-i]camptothecin-2-one;
29) 7-ethyl-2-imino-thiazolidino[4,5-i]camptothecin; and
30) 7-ethyl-2-methylimino-thiazolidino[4,5-i]camptothecin.

We claim:

1. A hexacyclic camptothecin compound of the formula (Ia)

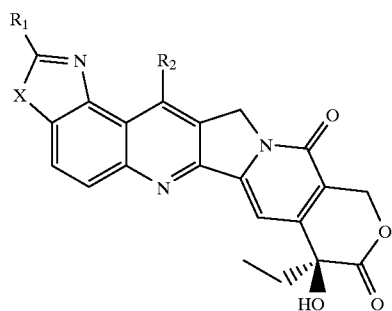

wherein:

$R_1$ is hydrogen;

optionally substituted $C_1$–$C_6$ alkyl;

$C_3$–$C_7$ cycloalkyl;

optionally substituted phenyl;

—$NR_3R_4$, wherein $R_3$ and $R_4$ are, each independently:
hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; or $R_3$ and $R_4$, combined together with the nitrogen atom to which they are linked, form a 3–7 membered, saturated or unsaturated, optionally substituted, heteromonocyclic ring;

—$OR_5$, wherein $R_5$ is hydrogen, optionally substituted $C_1$–$C_6$ alkyl $C_3$–$C_7$ cycloalkyl, optionally substituted phenyl, $C_1$–$C_6$ alkanoyl, optionally substituted benzoyl, optionally substituted $C_1$–$C_6$ alkoxycarbonyl or benzyloxycarbonyl; and —$SR_6$, wherein $R_6$ is hydrogen, optionally substituted $C_1$–$C_6$ alkyl, $C_3$–$C_7$ cycloalkyl, optionally substituted phenyl, $C_1$–$C_6$ alkanoyl, optionally substituted benzoyl, optionally substituted $C_1$–$C_6$ alkoxycarbonyl or benzyloxycarbonyl;

$R_2$ is hydrogen;

$C_1$–$C_6$ alkyl; $C_3$–$C_7$ cycloalkyl; and phenyl $C_1$–$C_6$ alkyl; and

X is an oxygen atom;

a sulfur atom; or

—$NR_7$—, wherein $R_7$ is:

hydrogen, optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; optionally substituted $C_1$–$C_6$ alkylsulfonyl; or optionally substituted $C_6$–$C_{10}$ arylsulfonyl;

or a pharmaceutically acceptable salt thereof;

or a hexacyclic camptothecin compound of the formula (Ib):

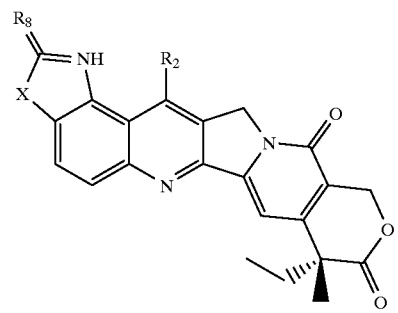

wherein:

$R_8$ is an oxygen atom;

a sulfur atom; or

=$NR_9$, wherein $R_9$ is:

hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl;

$R_2$ is hydrogen; $C_1$–$C_6$ alkyl; $C_3$–$C_7$ cycloalkyl; and phenyl $C_1$–$C_6$ alkyl; and X is an oxygen atom;

a sulfur atom; or

—$NR_7$—, wherein $R_7$ is:

hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; optionally substituted $C_1$–$C_6$ alkylsulfonyl; or optionally substituted $C_6$–$C_{10}$ arylsulfonyl;

or a pharmaceutically acceptable salt thereof.

2. The hexacyclic camptothecin compound of claim 1, wherein in the formula (Ia):

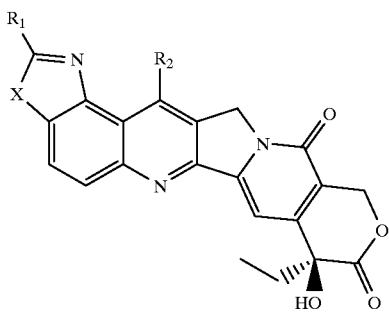

(Ia)

R₁ is hydrogen;

$C_1$–$C_6$ alkyl;

optionally substituted phenyl; or

—NR₃R₄, wherein R₃ and R₄ are, each independently: hydrogen; $C_1$–$C_6$ alkyl; or $C_1$–$C_6$ alkanoyl;

R₂ is hydrogen; or $C_1$–$C_6$ alkyl;

X is an oxygen atom; or a sulfur atom;

or a pharmaceutically acceptable salt thereof.

3. The hexacyclic camptothecin compound of claim 1, wherein in the formula (Ib):

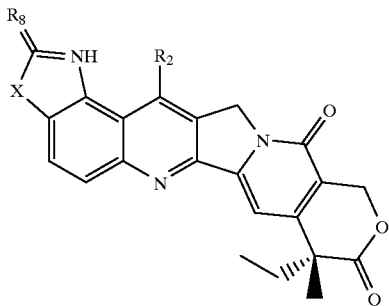

(Ib)

R₈ is oxygen; or

=NR₉, wherein R₉ is:

hydrogen; $C_1$–$C_6$ alkyl; or $C_1$–$C_6$ alkanoyl;

R₂ is hydrogen; and

X is an oxygen atom; or or a pharmaceutically acceptable salt thereof.

4. The hexacyclic camptothecin of claim 1, which is oxazolo[4,5-i]camptothecin;

2-methyl-oxazolo[4,5i]camptothecin;

2-butyl-oxozolo[4,5-i]camptothecin; 2-phenyl-oxazolo[4,5-i]camptothecin;

7-ethyl-oxazolo[4,5-i]camptothecin; 7-ethyl-2-methyl-oxazolo[4,5-i]camptothecin;

7-ethyl-2-butyl-oxazolo[4,5-i]camptothecin;

7-ethyl-2-phenyl-oxazolo oxazolo[4,5-i]camptothecin; thiazolo[4,5-i]camptothecin;

2-methyl-thiazolo[4,5-i]camptothecin; 2-butyl-thiazolo[4,5-i]camptothecin;

2-phenyl-thiazolo[4,5-i]camptothecin; 2-amino-thiazole[4,5-i]camptothecin;

2-acetamido-thiazolo[4,5-i]camptothecin; 7-ethyl-thiazolo[4,5-i]camptothecin;

7-ethyl-2-methyl-thiazolo [4,5-i]camptothecin; 7-ethyl-2-butyl-thiazolo[4,5-i]camptothecin;

or 7-ethyl-2-phenyl-thiazolo[4,5-i]camptothecin; or a pharmaceutically acceptable salt of any of the above.

5. The hexacyclic camptothecin compound of claim 1, which is oxazolidino[4,5-i]camptothecin-2-one;

2-imino-oxazolidino[4,5-i]camptothecin;

2-methylimino-oxazolidino[4,5-i]camptothecin;

7-ethyl-oxazolidino[4,5-i]camptothecin-2-one;

7-ethyl-2-imino-oxazolidino[4,5-i]camptothecin;

7-ethyl-2-methylimino-oxazolidino[4,5-i]camptothecin;

thiazolidino[4,5-i]camptothecin-2-one;

2-imino-thiazolidino [4,5-i]camptothecin;

2-methylimino-thiazolidino[4,5-i]camptothecin;

7-ethyl-thiazolidino [4,5-i]camptothecin-2-one;

7-ethyl-2-imino-thiazolidino[4,5-i]camptothecin; or 7-ethyl-2-methylimino-thiazolidino[4,5-i]camptothecin;

or a pharmaceutically acceptable salt of any of the above.

6. A process for preparing the hexacyclic camptothecin compound of formula (Ia) or (Ib) or a pharmaceutically acceptable salt of either of claim 1, which process comprises:

1) reducing a compound of formula (II):

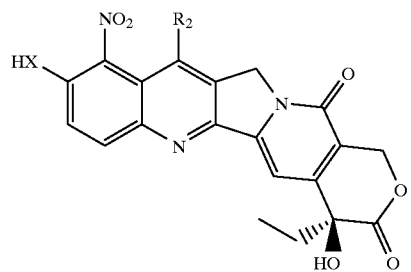

(II)

wherein:

R₂ is hydrogen; $C_1$–$C_6$ alkyl; $C_3$–$C_7$ cycloalkyl; and phenyl $C_1$–$C_6$ alkyl; and X is an oxygen atom;

a sulfur atom; or

—NR₇—, wherein R₇ is:

hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or a benzyloxycarbonyl; an optionally substituted $C_1$–$C_6$ alkylsulfonyl; or optionally substituted $C_6$–$C_{10}$ arylsulfonyl;

to obtain a compound of the formula (III):

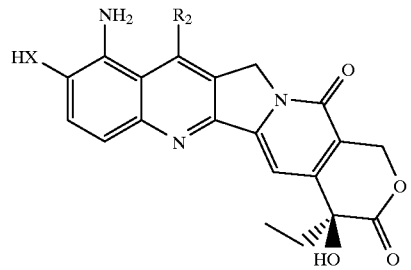

(III)

wherein

R₂ and X are as defined above; and 2) either a) reacting a compound of the formula (III) with a compound of the formula (IV):

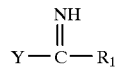   (IV)

wherein:

$R_1$ is hydrogen;

optionally substituted $C_1$–$C_6$ alkyl;

$C_3$–$C_7$ cycloalkyl;

optionally substituted phenyl;

—$NR_3R_4$, wherein $R_3$ and $R_4$ are, each independently, hydrogen, optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; or $R_3$ and $R_4$, combined together with the nitrogen atom to which they are linked, form a 3–7 membered, saturated or unsaturated, optionally substituted, heteromonocyclic ring;

—$OR_5$, wherein $R_5$ is hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; and —$SR_6$ group, wherein $R_6$ is hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; and Y is a leaving group;

to obtain a compound of the formula (Ia) as defined in claim 1; or b) reacting a compound of the formula (III) with a compound of the formula (V)

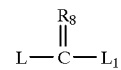   (V)

wherein:

$R_8$ is an oxygen atom;

a sulfur atom; or

=$NR_9$, wherein $R_9$ is hydrogen; optionally substituted $C_1$–$C_6$ alkyl; $C_3$–$C_7$ cycloalkyl; optionally substituted phenyl; $C_1$–$C_6$ alkanoyl; optionally substituted benzoyl; optionally substituted $C_1$–$C_6$ alkoxycarbonyl or benzyloxycarbonyl; and L and $L_1$, each independently, are leaving groups;

to obtain a compound of the formula (Ib) as defined in claim 1.

7. A pharmaceutical composition, comprising a pharmaceutically acceptable carrier and, as an active substance, an effective amount of one or more compounds of claim 1.

8. A method of treating leukemia or solid tumors in a mammal, which comprises administering to a mammal in nee thereof, an effective amount of one or more compounds of claim 1.

9. The method of claim 8, wherein said mammal is human.

10. The method of claim 8, wherein said solid tumor is a colon or rectal tumor.

* * * * *